United States Patent [19]

Asano et al.

[11] Patent Number: 5,116,426

[45] Date of Patent: May 26, 1992

[54] METHOD OF CLEANING A SUBSTRATE USING A DICHLOROPENTAFLUOROPROPANE

[75] Inventors: Teruo Asano, Yokohama; Naohiro Watanabe, Chiba; Kazuki Jinushi, Ichihara; Shunichi Samejima, Tokyo, all of Japan

[73] Assignee: Asaki Glass Company Ltd., Tokyo, Japan

[21] Appl. No.: 602,041

[22] Filed: Oct. 25, 1990

Related U.S. Application Data

[63] Continuation of Ser. No. 369,769, Jun. 22, 1989.

[30] Foreign Application Priority Data

| Jun. 22, 1988 | [JP] | Japan | 63-152271 |
| Jun. 22, 1988 | [JP] | Japan | 63-152272 |
| Jun. 22, 1988 | [JP] | Japan | 63-152273 |
| Jun. 22, 1988 | [JP] | Japan | 63-152274 |
| Jun. 22, 1988 | [JP] | Japan | 63-152275 |
| Jun. 22, 1988 | [JP] | Japan | 63-152276 |
| Jun. 22, 1988 | [JP] | Japan | 63-152277 |

[51] Int. Cl.⁵ .................. C23G 5/028; C23G 5/032
[52] U.S. Cl. .................. 134/40; 252/162; 252/165; 252/166; 252/170; 252/191
[58] Field of Search .......... 252/162, 165, 166, 171, 252/170; 134/40

[56] References Cited

U.S. PATENT DOCUMENTS

| 3,080,430 | 3/1963 | Cohen et al. | 260/653 |
| 3,336,189 | 4/1967 | Regan et al. | 167/52 |
| 3,377,392 | 4/1968 | Boudakian et al. | 260/653 |
| 3,804,769 | 4/1974 | Lomas | 252/171 |
| 4,491,531 | 1/1985 | Bargigia et al. | 252/153 |
| 4,770,714 | 9/1988 | Buchwald et al. | 134/40 |
| 4,828,751 | 5/1989 | Kremer | 252/171 |
| 4,947,881 | 8/1990 | Magid et al. | 134/40 |

FOREIGN PATENT DOCUMENTS 2128555 3/1972 France.

OTHER PUBLICATIONS

Journal of Fluorine Chemistry, vol. 13, No. 3, Mar. 1979, pp. 209-223, Elsevier Sequoia S. A., Lausanne, CH; R. D. Bagnall et al., "New inhalation anaesthetics: IV Gluorinated propanes".

Research Disclosure, No. 146, Jun. 1976, p. 13, abstract No. 14623, Hampshire GB; E. I. Du Pont de Nemours: "Hydrogen-containing chlorofluorocarbons".

Chemical Abstracts, vol. 110, 1989, p. 638, abstract No. 114259m, "Disubstituted polyfluoroalkenes".

Australian Office Action for Patent Application 36685/89.

Primary Examiner—Prince Willis, Jr.
Assistant Examiner—J. Silbermann
Attorney, Agent, or Firm—Oblon, Spivak, McClelland, Maier & Neustadt

[57] ABSTRACT

A method for cleaning a surface of a substrate which comprises treating the surface with a dichloro-pentafluoro-propane solvent. The method is specifically directed to the use of 1,1-dichloro-2,2,3,3,3-pentafluoro propane and 1,3-dichloro-1,1,2,2,3-pentafluoropropane as the cleaning solvent.

2 Claims, No Drawings

METHOD OF CLEANING A SUBSTRATE USING A DICHLOROPENTAFLUOROPROPANE

This application is a continuation of application Ser. No. 07/369,769, filed on Jun. 22, 1989, now abandoned.

TECHNICAL FIELD

The present invention relates to novel halogenated hydrocarbon solvents and use thereof.

BACKGROUND ART 1,1,2-Trichloro-1,2,2-trifluoroethane (hereinafter referred to simply as R113) is non-flammable, nonexplosive and stable with low toxicity and as such, is widely used as a cleaning agent for a flux employed in the assembling process of electronic parts or precision machine parts or for cutting oils, or as a cleaning agent for clothings such as fur coats or suits. Further, R113 is widely used for removing deposited water after the washing treatment with water of liquid crystal display device parts, electronic parts or precision machine parts. On the other hand, a rinsing agent such as trichloroethylene is used to remove a resist-removing agent deposited on a wafer. 1,1,1-Trichloroethane is used as a cleaning agent to remove a buffing agent deposited on precision metal parts or decorative parts after the buffing treatment thereof. Further, 1,1,1-trichloroethane is used for developing a resist in the preparation of a printed circuit board or a semiconductor circuit, and methylene chloride or perchloroethylene is used for removing the resist after etching treatment.

In spite of its various merits, R113 has been found to destroy ozone in the stratosphere, which in turn brings about a skin cancer. On the other hand, methylene chloride, trichloroethylene, perchloroethylene and 1,1,1-trichloroethane are likely to bring about a pollution of underground water, and it is required to minimize the amount of their use.

Under these circumstances, it is an object of the present invention to solve such problems and to provide a novel halogenated hydrocarbon solvent as a substitute for the conventional solvents.

DISCLOSURE OF THE INVENTION

The present invention provides a halogenated hydrocarbon solvent consisting essentially of a hydrogencontaining chlorofluoropropane having a difluoromethylene group represented by the formula:

$$CH_aCl_bF_cCF_2CH_xCl_yF_z \quad (I)$$

wherein $a+b+c=3$, $x+y+z=3$, $a+x \geq 1$, $b+y \geq 1$, and $0 \leq a, b, c, x, y, z \leq 3$.

Now, the present invention will be described in detail with reference to the preferred embodiments.

Specific examples of the compound of the formula I are as follows:

CClF$_2$CF$_2$CHCl$_2$ (R224ca)
CCl$_2$FCF$_2$CHClF (R224cb)
CF$_3$CF$_2$CHCl$_2$(R225ca)
CClF$_2$CF$_2$CHClF(R225cb)
CClF$_2$CF$_2$CH$_2$Cl(R234cc)
CHF$_2$CF$_2$CHClF (R235ca)
CH$_2$CF$_2$CCl$_2$F(R243cc)
CHF$_2$CF$_2$CH$_2$Cl(R244ca)
CH$_2$ClCF$_2$CH$_2$Cl(R252ca)
CHCl$_2$CF$_2$CH$_3$(R252cb)
CH$_3$CF$_2$CH$_2$Cl(R262ca)
CHF$_2$CF$_2$CCl$_2$F(R225cc)
CHClFCF$_2$CHClF(R234ca)
CHF$_2$CF$_2$CHCl$_2$(R234cb)
CH$_2$FCF$_2$CCl$_2$F(R234cd)
CF$_3$CF$_2$CH$_2$Cl(R235cb)
CClF$_2$CF$_2$CH$_2$F(R235cc)
CH$_2$ClCF$_2$CHClF(R243ca)
CH$_2$FCF$_2$CHCl$_2$(R b 243cb)
CH$_2$FCF$_2$CHClF(R244cb)
CClF$_2$CF$_2$CH$_3$(R244cc)
CH$_2$FCF$_2$CH$_2$Cl(R253ca)
CH$_3$CG$_2$CHClF(R253cb)
CF$_3$CF$_2$CHClF(R226ca)
CClF$_2$CF$_2$CHF$_2$(R226cb)
CCl$_3$CF$_2$CHCl$_2$(R222c)
CCl$_2$FCF$_2$CHCl$_2$(R223ca)
CCl$_3$CF$_2$CHClF(R223cb)
CCl$_3$CF$_2$CHF$_2$(R224cc)
CHCl$_2$CF$_2$CHCl$_2$(R232ca)
CCl$_3$CF$_2$CH$_2$Cl(R232cb)
CCl$_2$FCF$_2$CH$_2$Cl(R233cb)
CHCl$_2$CF$_2$CHClF(R233ca)
CCl$_3$CF$_2$CH$_2$F(R233cc)
CCl$_3$CF$_2$CH$_3$(R242cb)
CHCl$_2$CF$_2$CH$_2$Cl(R242ca)

The compounds of the present invention represented by the formula I may be used alone or in combination as a mixture of two or more. They are useful as various cleaning agents including a cleaning agent for dry cleaning, a degreasing agent, a cleaning agent for removing a buffing agent, a flux cleaning agent and a rinsing agent, or as a resist developing agent or a resist removing agent, or as a solvent for removing deposited water. They are useful also for the following various purposes:

As a solvent for extracting nicotine contained in tobacco leaves or for extracting pharmeceutical substances from animal or plants, as a diluent for various chemical agents including a coating material, a releasing agent, a water and oil repellant, a moistureproof coating, a water-proofing agent, a lustering agent and an antistatic agent, to disperse or dissolve them to facilitate their application to the respective objects, as an aerosol solvent for dissolving a chemical agent or an active agent contained in an aerosol of e.g. a coating material, an insecticide, a pharmaceutical, a sweat-preventing agent, a deodorant, a hair conditioner or a cosmetic, and as an insulating medium for insulating and cooling e.g. an oil-filled transformer or a gas-insulated transformer.

When the compounds of the present invention are employed for the above-mentioned various purposes, it is preferred to incorporate various other compounds depending upon the particular purposes.

For example, an organic solvent such as a hydrocarbon, an alcohol, a ketone, a chlorinated hydrocarbon, an ester or an aromatic compound, or a surfactant, may be incorporated to improve the cleaning effects in the use as a cleaning solvent or to improve the effects in other uses. Such an organic solvent may be incorporated usually in an amount of from 0 to 80% by weight, preferably from 0 to 50% by weight, more preferably from 10 to 40% by weight, in the composition. The surfactant may be used usually in an amount of from 0 to 10% by weight, preferably from 0.1 to 5% by weight, more preferably from 0.2 to 1% by weight.

The hydrocarbon is preferably a linear or cyclic saturated or unsaturated hydrocarbon having from 1 to 15 carbon atoms and is usually selected from the group consiting of n-pentane, isopentane, n-hexane, isohexane, 2-methylpentane, 2,2-dimethylbutane, 2,3-dimethylbutane, n-heptane, isoheptane, 3-methylhexane, 2,4-dimethylpentane, n-octane, 2-methylheptane, 3-methylheptane, 4-methylheptane, 2,2-dimethylhexane, 2,5-dimethylhexane, 3,3-dimethylhexane, 2-methyl-3-ethylpentane, 3-methyl-3-ethylpentane, 2,3,3-trimethylpentane, 2,3,4-trimethylpentane, 2,2,3-trimethylpentane, isooctane, nonane, 2,2,5-trimethylhexane, decane, dodecane, 1-pentene, 2-pentene, 1-hexene, 1-octene, 1 nonene, 1-decene, cyclopentane, methylcyclopentane, cyclohexane, methylcyclohexane, ethylcyclohexane, bicyclohexane, cyclohexene, α-pinene, dipentene, decalin, tetralin, amylene and amylnaphthalene. More preferred are n-pentane, n-hexane, cyclohexane and n-heptane.

The alcohol is preferably an aliphatic or cyclic saturated or unsaturated alcohol having from 1 to 17 carbon atoms and is usually selected from the group consisting of methanol, ethanol, n-propyl alcohol, isopropyl alcohol, n-butyl alcohol, sec butyl aclohol, isobutyl alcohol, tert-butyl aclohol, pentyl alcohol, sec amyl alcohol, 1-ethyl-1-propanol, 2-methyl-1-butanol, isopentyl alcohol, tert-pentyl alcohol, 3-methyl-2-butanol, neopentyl alcohol, 1-hexanol, 2-methyl 1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 3,5,5-trimethyl-1-hexanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, 4-methylcyclohexanol, α-terpineol, abietinol, 2,6-dimethyl-4-heptanol, trimethyl nonylalcohol, tetradecyl alcohol and heptadecyl alcohol. More preferred are methanol, ethanol and isopropyl alcohol.

The ketone is preferably represented by one of the formulas

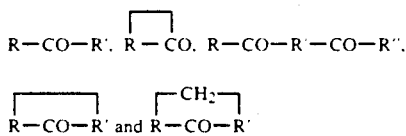

wherein each of R, R' and R" is a saturated or unsaturated hydrocarbon group having from 1 to 9 carbon atoms and is usually selected from the group consisting of acetone, methyl ethyl ketone, 2-pentanone, 3-pentanone, 2-hexanone, methyl-n butyl ketone, methyl butyl ketone, 2-heptanone, 4-heptanone, diisobutyl ketone, acetonitrile, acetone, mesityl oxide, phorone, methyl n-amyl ketone, ethyl butyl ketone, methyl hexyl ketone, cyclohexanone, methylcyclohexanone, isophorone, 2,4 pentanedione, diacetone alcohol, acetophenone and fenchone. More preferred are acetone and methyl ethyl ketone.

The chlorinated hydrocarbon is preferably a satuarted or unsaturated chlorinated hydrocarbon having 1 or 2 carbon atoms and is usually selected from the group consisting of methylene chloride, carbon tetrachloride, 1,1 dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, 1,1-dichloroethylene, 1,2-dichloroethylene, trichloroethylene and tetrachloroethylene. More preferred are methylene chloride, 1,1,1-trichloroethane, trichloroethylene and tetrachloroethylene.

The surfactant for a solvent for removing deposited water is preferably selected from the group consisting of a polyoxyethylene alkyl ether, a polyoxyethylene polyoxypropylene alkyl ether, a polyoxyethylene alkyl ester, a polyoxyethylene polyoxypropylene alkyl ester, a polyoxyethylene alkyl phenol, a polyoxyethylene polypropylene alkyl phenol, a polyoxyethylene sorbitan ester, a polyoxyethylene polyoxypropylene sorbitan ester, caprylic acid caprylamine and a polyoxyethylene alkylamide. More preferred are caprylic acid caprylamine and a polyoxyethylene alkylamide. As the surfactant of a cleaning agent for dry cleaning, various surfactants including non ionic, cationic, anionic and amphoteric surfactants may be employed. It is preferably selected from the group consisting of a linear alkyl benzene sulfonate, a long chain alcohol sulfate, a polyoxyethylene ether sulfate, a polyoxyethylene alkyl ether phosphate, a polyoxyethylene alkyl ether sulfate, a polyoxyethylene alkylphenyl ether phosphate, an α-olefin sulfonate, an alkylsulfosuccinate, a polyoxyethylene alkyl ether, a polyoxyethylene alkyl ester, a polyoxyethylene alkylallyl ether, a fatty acid diethanolamide, a polyoxyethylene alkylamide, a sorbitan fatty acid ester, a polyoxyethylene fatty acid ester, a quaternary ammonium salt, a hydroxysulfobetaine, a polyoxyethylenelauryl ether, a polyoxyethylenelauryl ether sodium sulfate, sodium dodecylbenzene sulfonate and a higher alcohol sodium sulfate. More preferred are a polyoxyethylenelauryl ether, a polyoxyethylenelauryl ether sodium sulfate, sodium dodecylbenzene sulfonate and a higher alcohol sodium sulfate.

The aromatic compound is preferably a benzene derivative or a naphthalene derivative and is usually selected from the group consisting of benzene, toluene, xylene, ethylbenzene, isopropylbenzene, diethylbenzene, sec-butylbenzene, triethylbenzene, diisopropylbenzene, styrene, an alkylbenzene sulfonic acid, phenol, mesitylene, naphthalene, tetralin, butylbenzene, p-cymene, cyclohexylbenzene, pentylbenzene, dipentylbenzene, dodecylbenzene, biphenyl, o-cresol, m-cresol and xylenol. More preferred are an alkylbenzene sulfonic acid and phenol.

The ester is preferably represented by one of the following formulas:

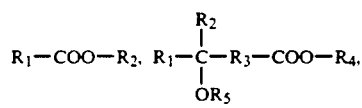

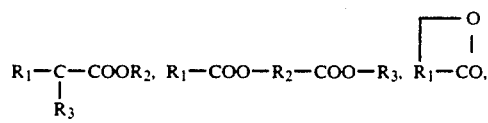

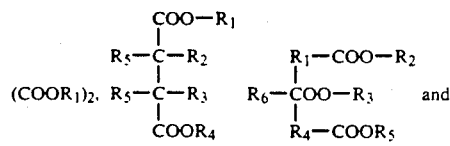

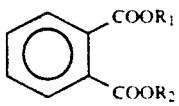

wherein each of $R_1$, $R_2$, $R_3$, $R_4$, $R_5$ and $R_6$ is H, OH or a saturated or unsaturated hydrocarbon group having from 1 to 19 carbon atoms. Specifically, it is selected from the group consisting of methyl formate, ethyl formate, propyl formate, butyl formate, isobutyl formate, pentyl formate, methyl acetate, ethyl acetate, propyl acetate, isopropyl acetate, butyl acetate, isobutyl acetate, secbutyl acetate, pentyl acetate, isopentyl acetate, 3-methoxybutyl acetate, sec hexyl acetate, 2-ethylbutyl acetate, 2-ethylhexyl acetate, cyclohexyl acetate, benzyl acetate, methyl propionate, ethyl propionate, butyl propionate, isopentyl propionate, methyl butyrate, ethyl butyrate, butyl butyrate, isopentyl butyrate, isobutyl isobutyrate, ethyl 2-hydroxy-2-methylpropionate, butyl stearate, methyl benzoate, ethyl benzoate, propyl benzoate, butyl benzoate, isopentyl benzoate, benzyl benzoate, ethyl abietate, benzyl abietate, bis-2-ethylhexyl adipate, γ-butyrolactone, diethyl oxalate, dibutyl oxalate, dipentyl oxalate, diethyl malonate, dimethyl maleate, diethyl maleate, dibutyl maleate, dibutyl tertarate, tributyl citrate, dibutyl sebacate, bis-2-ethylhexyl cebacate, dimethyl phthalate, diethyl phthalate, dibutyl phthalate, bis-2-ethylhexyl phthalate and dioctyl phthalate. More preferred are methyl acetate and ethyl acetate.

A chlorofluorinated hydrocarbon other than the compound of the formula I may be incorporated to the compound of the present invention. When azeotropy or pseudoazeotropy exists with a composition obtained by the combination of the compound of the present invention with other compound, it is preferred to use them under an azeotropic or pseudoazeotropic condition so that there will be no variation in the composition when used by recycling, or no substantial change from the conventional technique will be required.

The cleaning agent for dry cleaning of the present invention may contain various additives such as an antistatic agent, a softening agent, a stain removing agent, a flame retardant, a water and oil repellant or a stabilizer. As the stabilizer, various types which are commonly used for the cleaning agent for dry cleaning, may be employed, including nitroalkanes, epoxides, amines or phenols.

Various cleaning additives or stabilizers may be incorporated also to the degreasing agent, the cleaning agent for the removal of a buffing agent, or a flux cleaning agent. In the case of the cleaning agent for removing a buffing agent, water may further be incorporated. As the cleaning method, wiping by manual operation, dipping, spraying, shaking, supersonic cleaning, steam cleaning or any other conventional method may be employed.

When it is necessary to stabilize the rinsing agent, it is preferred to employ a nitroalkane such as nitromethane, nitroethane or nitropropane, or a cyclic ether such as propylene oxide, 1,2-butylene oxide, 2,3-butylene oxide, epichlorohydrin, styrene oxide, butyl glycidyl ether, phenyl glycidyl ether, glycidol, 1,4-dioxane, 1,3,5-trioxane, 1,3-dioxolan, dimethoxymethane or 1,2-dimethoxyethane, in an amount of from 0.001 to 5.0 % by weight, in combination.

There is no particular restriction as to the resist to be developed or to be removed by the present invention. The resist may be a positive or negative resist for exposure, a resist for exposure with far ultraviolet rays or a resist for exposure with X-rays or with electron beams. The resist for exposure with light includes a quinone diazide type having phenol and cresol novolak resin as the base materials, a cyclic rubber type having cis-1,4-polyisoprene as the essential component and a polycinnamate type. Likewise, the resist for exposure with far ultraviolet rays includes polymethyl methacrylate and polymethylisopropenyl ketone. The resist for exposure with electron beam or with X-rays includes poly(methyl methacrylate), a glycidyl methacrylate-ethyl acrylate copolymer, and a methyl methacrylate-methacrylic acid copolymer.

For the removal of deposited water by means of the solvent for removing deposited water according to the present invention, it is possible to employ a spraying or showering method or a dipping method in a cool bath, a warm bath, a steam bath or a supersonic bath, or a dipping method with a combination of these baths.

The insulating medium of the present invention may be used in combination with a mineral oil type insulating medium, a completely halogenated hydrocarbon type insulating medium or a silicone oil insulating medium, which is commonly employed in this field. Further, for the purpose of stabilization, a stabilizing agent such as a phosphite compound, a phosphine sulfide compound or a glycidyl ether compound may be incorporated, or a phenol or amine antioxidant may be used in combination.

Now, the present invention will be described in further detail with reference to Examples. However, it should be understood that the present invention is by no means restricted to such specific Examples.

EXAMPLES 1-1 to 1-16

Cleaning tests for cleaning power were conducted by using the dry cleaning agents as identified in Table 1. A soiled cloth (5×5 cm) of wool having carbon soil fixed by a Yukagaku Kyokai method was put into a Scrub-O-meter cleaning machine and washed at 25° C. for 25 minutes, whereupon the cleaning effects were measured by an ELREPHO photoelectric reflection meter. The results are shown in Table 1.

TABLE 1

| Example No. | Dry cleaning agents | Cleaning effects |
|---|---|---|
| Example 1-1 | R225ca (100) | ⊚ |
| Example 1-2 | R225cb (100) | ⊚ |
| Example 1-3 | R224ca (100) | ⊚ |
| Example 1-4 | R224cb (100) | ⊚ |
| Example 1-5 | R235ca (100) | ⊚ |
| Example 1-6 | R234cc (100) | ⊚ |
| Example 1-7 | R244ca (100) | ⊚ |
| Example 1-8 | R243cc (100) | ⊚ |
| Example 1-9 | R252ca (100) | ⊚ |
| Example 1-10 | R252cb (100) | ⊚ |
| Example 1-11 | R262ca (100) | ⊚ |
| Example 1-12 | R225ca(75)/n-heptane(25) | ⊚ |
| Example 1-13 | R225ca(75)/ethanol(25) | ⊚ |
| Example 1-14 | R225ca(75)/perchloroethylene(25) | ⊚ |
| Example 1-15 | R225ca(75)/acetone(25) | ⊚ |
| Example 1-16 | R225ca(75)/sodium dodecyl- | ⊚ |

TABLE 1-continued

| Example No. | Dry cleaning agents | Cleaning effects |
|---|---|---|
| | benzene sulfonate(25) | |

The value in the bracket ( ) represents a proportion (% by weight)
Evaluation Standards
ⓒ Stain satisfactorily removed
○ Stain substantially satisfactorily removed
△ Stain slightly remained
X Stain substantially remained

EXAMPLES 2-1 to 2-16

Cleaning tests of cutting oil were conducted by using the degreasing agents as identified in Table 2.

A test piece (25 mm×30 mm×2 mm) of SUS-304 was dipped in spindle oil, and then dipped in the degreasing agent for 5 minutes. Then, the test piece was taken out, and the state of the spindle oil remaining on the surface of the test piece was visually evaluated. The results are shown in Table 2.

TABLE 2

| Example No | Degreasing agent | Degreasing effects |
|---|---|---|
| Example 2-1 | R225ca (100) | ⓒ |
| Example 2-2 | R225cb (100) | ⓒ |
| Example 2-3 | R224ca (100) | ⓒ |
| Example 2-4 | R224cb (100) | ⓒ |
| Example 2-5 | R235ca (100) | ⓒ |
| Example 2-6 | R234cc (100) | ⓒ |
| Example 2-7 | R244ca (100) | ⓒ |
| Example 2-8 | R243cc (100) | ⓒ |
| Example 2-9 | R252ca (100) | ⓒ |
| Example 2-10 | R252cb (100) | ⓒ |
| Example 2-11 | R262ca (100) | ⓒ |
| Example 2-12 | R225ca(75)/n-heptane(25) | ⓒ |
| Example 2-13 | R225ca(75)/ethanol(25) | ⓒ |
| Example 2-14 | R225ca(75)/acetone(25) | ⓒ |
| Example 2-15 | R225ca(75)/trichloroethylene(25) | ⓒ |
| Example 2-16 | R225ca(75)/ethyl acetate (25) | ⓒ |

The value in the bracket ( ) represents a proportion (% by weight)
Evaluation Standards
ⓒ Satisfactorily degreased
○ Substantially satisfactorily degreased
△ Oil slightly remained
X Oil substantially remained

EXAMPLES 3-1 to 3-16

Tests for removing a buffing agent were conducted by using the cleaning agents for removing a buffing agent as identified in FIG. 3.

A wrist watch frame was polished with a buffing agent (GS-1 manufactured by Soken Kogyo K.K.) and then immersed in the cleaning agent for removing a buffing agent, and a supersonic wave was applied thereto for 3 minutes. Then, it was taken out and inspected for the removal of the buffing agent. The results are shown in Table 3.

TABLE 3

| Example No. | Cleaning agent for removing a buffing agent | Results |
|---|---|---|
| Example 3-1 | R225ca (100) | ⓒ |
| Example 3-2 | R225cb (100) | ⓒ |
| Example 3-3 | R224ca (100) | ⓒ |
| Example 3-4 | R224cb (100) | ⓒ |
| Example 3-5 | R235ca (100) | ⓒ |
| Example 3-6 | R234cc (100) | ⓒ |
| Example 3-7 | R244ca (100) | ⓒ |
| Example 3-8 | R243cc (100) | ⓒ |
| Example 3-9 | R252ca (100) | ⓒ |
| Example 3-10 | R252cb (100) | ⓒ |
| Example 3-11 | R262ca (100) | ⓒ |
| Example 3-12 | R225ca(75)/n-hexane(25) | ⓒ |
| Example 3-13 | R225ca(75)/ethanol(25) | ○ |
| Example 3-14 | R225ca(75)/acetone(25) | ○ |
| Example 3-15 | R225ca(75)/1,1,1-trichloroethane(25) | ⓒ |
| Example 3-16 | R225ca(75)/ethyl acetate (25) | ⓒ |
| Comparative Example 3-1 | 1,1,1-trichloroethane (100) | ○ |

The value in the bracket ( ) represents a proportion (% by weight)
Evaluation Standards
ⓒ Buffing agent satisfactorily removed
○ Buffing agent substantially satisfactorily removed.
△ Buffing agent slightly remained
X Buffing agent substantially remained

EXAMPLES 4-1 to 4-15

Flux cleaning tests were conducted by using the flux cleaning agents as identified in Table 4.

A flux (Tamura F-Al-4, manufactured by Kabushiki Kaisha Tamura Seisakusho) was coated on the entire surface of a printed circuit board (a copper-clad laminate) and baked in an electric furnace at 200° C. for 2 minutes. Then, the board was immersed in the flux cleaning agent for one minute. The degree of the removal of the flux is shown in Table 4.

TABLE 4

| Example No. | Flux cleaning agents | Cleaning effects |
|---|---|---|
| Example 4-1 | R225ca (100) | ⓒ |
| Example 4-2 | R225cb (100) | ⓒ |
| Example 4-3 | R224ca (100) | ⓒ |
| Example 4-4 | R224cb (100) | ⓒ |
| Example 4-5 | R235ca (100) | ⓒ |
| Example 4-6 | R234cc (100) | ⓒ |
| Example 4-7 | R244ca (100) | ⓒ |
| Example 4-8 | R243cc (100) | ⓒ |
| Example 4-9 | R252ca (100) | ⓒ |
| Example 4-10 | R252cb (100) | ⓒ |
| Example 4-11 | R262ca (100) | ⓒ |
| Example 4-12 | R225ca(75)/n-heptane(25) | ⓒ |
| Example 4-13 | R225ca(75)/methanol(25) | ⓒ |
| Example 4-14 | R225ca(75)/acetone(25) | ⓒ |
| Example 4-15 | R225ca(75)/trichloroethylene(25) | ⓒ |

The value in the bracket ( ) represents a proportion (% by weight)
Evaluation Standards
ⓒ Flux satisfactorily removed.
○ Flux substantially satisfactorily removed.
△ Flux slightly remained.
X Flux substantially remained.

EXAMPLES 5-1 to 5-7

A positive resist (OFPR-800, manufactured by Tokyo Okasha) or a negative resist (OMR-83, manufactured by Tokyo Okasha) was coated on a silicon wafer, followed by etching treatment, then the silicon wafer was immersed in an o-dichlorobenzene type resist removing solution (resist removing solution-502, manufactured by Tokyo Okasha) at 120° C. for 10 minutes and then immersed in the rinsing agent as identified in Table 5 at 25° C. for 3 minutes. Further, it was immersed and cleaned in an IPA/MEK mixed solution and then in superpure water and then dried, whereupon the surface condition was inspected by a microscope.

TABLE 5

| Example No. | Rinsing agents | Proportions (wt %) | Results |
|---|---|---|---|
| Example 5-1 | R225ca | 100 | No fine particles detected on the surface |

TABLE 5-continued

| Example No | Rinsing agents | Proportions (wt %) | Results |
|---|---|---|---|
| Example 5-2 | R225cb | 100 | No fine particles detected on the surface |
| Example 5-3 | R242cc | 100 | No fine particles detected on the surface |
| Example 5-4 | R244ca | 100 | No fine particles detected on the surface |
| Example 5-5 | R262ca | 100 | No fine particles detected on the surface |
| Example 5-6 | R262ca Heptane | 90 10 | No fine particles detected on the surface |
| Example 5-7 | R244ca Heptane | 90 10 | No fine particles detected on the surface |

EXAMPLES 6-1 to 6-16

Resist developing tests were conducted by using the resist developing agents as identified in Table 6.

A printed circuit board (a copper-clad laminate) having a photoresist film (Laminer, manufactured by Dynachem Co.) laminated thereon, was exposed to have a predetermined circuit pattern and then developed with the resist developing agent, whereupon the surface was inspected by a microscope to see if the circuit pattern was properly formed. The results are shown in Table 6.

TABLE 6

| Example No. | Resist developing agent | Results of inspection |
|---|---|---|
| Example 6-1 | R225ca (100) | ⊚ |
| Example 6-2 | R225cb (100) | ⊚ |
| Example 6-3 | R224ca (100) | ⊚ |
| Example 6-4 | R224cb (100) | ⊚ |
| Example 6-5 | R235ca (100) | ⊚ |
| Example 6-6 | R234cc (100) | ⊚ |
| Example 6-7 | R244ca (100) | ⊚ |
| Example 6-8 | R243cc (100) | ⊚ |
| Example 6-9 | R252ca (100) | ⊚ |
| Example 6-10 | R252cb (100) | ⊚ |
| Example 6-11 | R262ca (100) | ⊚ |
| Example 6-12 | R225ca(75)/n-pentane(25) | ⊚ |
| Example 6-13 | R225ca(75)/ethanol(25) | ⊚ |
| Example 6-14 | R225ca(75)/acetone(25) | ⊚ |
| Example 6-15 | R225ca(75)/1,1,1-trichloroethane(25) | ⊚ |
| Example 6-16 | R225ca(75)/methyl acetate (25) | ⊚ |
| Comparative Example 6-1 | 1,1,1-trichloroethane (100) | ⊚ |

The value in the bracket ( ) represents a proportion (% by weight)
Evaluation Standards
⊚ Satisfactorily developed
○ Substantially satisfactorily developed
△ Slightly inferior
X Inferior

EXAMPLES 7-1 to 7-17

Resist removing tests were conducted by using the resist removing agents as identified in Table 7.

A printed circuit board (a copper-clad laminate) having a photoresist film (Laminer, manufactured by Dynachem Co.) laminated thereon, was subjected to exposure, development and etching treatments to form a printed circuit and then immersed in the resist removing agent at room temperature for 15 minutes. The board was taken out and inspected by a microscope to see the state of removal of the cured film. The results are shown in Table 7.

TABLE 7

| Example No. | Resist removing agent | Results |
|---|---|---|
| Example 7-1 | R225ca (100) | ⊚ |
| Example 7-2 | R225cb (100) | ⊚ |
| Example 7-3 | R224ca (100) | ⊚ |
| Example 7-4 | R224cb (100) | ⊚ |
| Example 7-5 | R235ca (100) | ⊚ |
| Example 7-6 | R234cc (100) | ⊚ |
| Example 7-7 | R244ca (100) | ⊚ |
| Example 7-8 | R243cc (100) | ⊚ |
| Example 7-9 | R252ca (100) | ⊚ |
| Example 7-10 | R252cb (100) | ⊚ |
| Example 7-11 | R262ca (100) | ⊚ |
| Example 7-12 | R225ca(75)/n-pentane(15) alkylbenzene sulfonic acid(10) | ⊚ |
| Example 7-13 | R225ca(75)/ethanol(15) alkylbenzene sulfonic acid(10) | ⊚ |
| Example 7-14 | R225ca(75)/acetone(15) phenol(10) | ⊚ |
| Example 7-15 | R225ca(75)/methylene chloride(15) phenol(25) | ⊚ |
| Example 7-16 | R225ca(75)/phenol(25) | ⊚ |
| Example 7-17 | R225ca(75)/methyl acetate (25) | ⊚ |
| Comparative Example 7-1 | Tetrachloroethylene(100) | ○ |
| Comparative Example 7-2 | o-Dichlorobenzene(100) | ○ |

The value in the bracket ( ) represents a proportion (% by weight)
Evaluation Standards
⊚ Resist satisfactorily removed
○ Resist substantially satisfactorily removed
△ Resist slightly remained
X Resist substantially remained

EXAMPLES 8-1 to 8-16

Tests for removing deposited water were conducted by using the solvents for removing deposited water as identified in Table 8.

A glass sheet of 30 mm×18 mm×5 mm was immersed in pure water and then immersed in the solvent for removing deposited water for 20 seconds. Then, the glass sheet was taken out and immersed in dry methanol, whereupon the state of removal of deposited water was determined by the increase the water content. The results are shown in Table 8.

TABLE 8

| Example No. | Solvents for removing deposited water | Effects for removing deposited water |
|---|---|---|
| Example 8-1 | R225ca (100) | ⊚ |
| Example 8-2 | R225cb (100) | ⊚ |
| Example 8-3 | R224ca (100) | ⊚ |
| Example 8-4 | R224cb (100) | ⊚ |
| Example 8-5 | R235ca (100) | ⊚ |
| Example 8-6 | R234cc (100) | ⊚ |
| Example 8-7 | R244ca (100) | ⊚ |
| Example 8-8 | R243cc (100) | ⊚ |
| Example 8-9 | R252ca (100) | ⊚ |
| Example 8-10 | R252cb (100) | ⊚ |
| Example 8-11 | R262ca (100) | ⊚ |
| Example 8-12 | R225ca(75)/methanol(25) | ⊚ |
| Example 8-13 | R225ca(75)/acetone(5) isopropyl alcohol(20) | ⊚ |
| Example 8-14 | R225ca(75)/trichloroethylene(5) ethanol(20) | ⊚ |
| Example 8-15 | R225ca(75)/n-heptane(15)/methanol(20) | ⊚ |
| Example 8-16 | R225ca(99.5)/caprylamine | ⊚ |

TABLE 8-continued

| Example No. | Solvents for removing deposited water | Effects for removing deposited water |
|---|---|---|
| | caprylic acid(0.5) | |

The value in the bracket ( ) represents a proportion (% by weight)
Evaluation Standards
◎ Deposited water satisfactorily removed
○ Deposited water substantially satisfactorily removed
△ Deposited water slightly remained
X Deposited water substantially remained

EXAMPLES 9-1 to 9-11

Tests for extracting nicotine contained in tobacco leaves were conducted by using the extraction solvent compositions of the present invention as identified in Table 9.

A predetermined amount of a tobacco sample (Hilite, commercial product) was put in a Soxhlet extractor, and refluxing was conducted by means of the extraction solvent composition of the present invention for 8 hours under heating. After the refluxing, the solvent was evapoarted to dryness, and the amount of extract was measured. The results are shown in Table 9. By using methanol as a comparative solvent, a similar test was conducted. The amount of extract in this case was evaluated to be 100, and the results of other tests were represented by relative values thereto.

As other Comparative Examples, similar tests were conducted with respect to acetone and hexane.

The evaporation residues of the respective tests were subjected to gas chromatography, whereby it was found that nicotine was contained in each residue.

TABLE 9

| | Extraction solvent compositions | Extraction rates |
|---|---|---|
| Example 9-1 | R224ca | 150 |
| Example 9-2 | R224cb | 150 |
| Example 9-3 | R225ca | 140 |
| Example 9-4 | R225cb | 140 |
| Example 9-5 | R234cc | 140 |
| Example 9-6 | R235ca | 150 |
| Example 9-7 | R243cc | 150 |
| Example 9-8 | R244ca | 160 |
| Example 9-9 | R252ca | 160 |
| Example 9-10 | R252cb | 150 |
| Example 9-11 | R262ca | 150 |
| Comparative Example 9-1 | Methanol | 100 |
| Comparative Example 9-2 | Acetone | 90 |
| Comparative Example 9-3 | Hexane | 90 |

EXAMPLES 10-1 to 10-51

By using the diluents as identified in Tables 10-1 to 10-3, a moisture-proof coating agent composed of a polyfluoroalkyl group-containing polymer was diluted. The diluted composition thus obtained was coated on the surface of a printed circuit board and dried in air to form a moisture-proof coating film on the surface of the printed circuit board. The dried state of this moisture-proof coating film was visually inspected. The results are shown in Tables 10-1 to 10-3.

TABLE 10-1

| | Diluents | Film forming properties |
|---|---|---|
| Example 10-1 | R224ca (100) | ◎ |
| Example 10-2 | R224cb (100) | ◎ |
| Example 10-3 | R225ca (100) | ◎ |
| Example 10-4 | R225cb (100) | ◎ |
| Example 10-5 | R234cc (100) | ◎ |
| Example 10-6 | R235cc (100) | ◎ |
| Example 10-7 | R243cc (100) | ◎ |
| Example 10-8 | R244ca (100) | ◎ |
| Example 10-9 | R252ca (100) | ◎ |
| Example 10-10 | R252cb (100) | ◎ |
| Example 10-11 | R262ca (100) | ◎ |
| Example 10-12 | R225ca(75)/n-heptane(25) | ◎ |
| Example 10-13 | R225ca(75)/ethanol(25) | ◎ |
| Example 10-14 | 225ca(75)/acetone(25) | ◎ |
| Example 10-15 | 225ca(75)/trichloroethylene(25) | ◎ |
| Example 10-15 | 225ca(75)/ethyl acetate(25) | ◎ |

The value in the bracket ( ) represents a proportion (% by weight)
Evaluation Standards
◎ Excellent
○ Good
△ Slight non-uniformity observed
X Substantial non-uniformity observed

TABLE 10-2

| | Diluents | Film forming properties |
|---|---|---|
| Example 10-17 | R225cc (100) | ◎ |
| Example 10-18 | R234ca (100) | ◎ |
| Example 10-19 | R234cb (100) | ◎ |
| Example 10-20 | R234cd (100) | ◎ |
| Example 10-21 | R235cb (100) | ◎ |
| Example 10-22 | R235cc (100) | ◎ |
| Example 10-23 | R243ca (100) | ◎ |
| Example 10-24 | R243cb (100) | ◎ |
| Example 10-25 | R244cb (100) | ◎ |
| Example 10-26 | R244cc (100) | ◎ |
| Example 10-27 | R253ca (100) | ◎ |
| Example 10-28 | R253cb (100) | ◎ |
| Example 10-29 | R244cb(75)/n-heptane(25) | ◎ |
| Example 10-30 | R244cb(75)/ethanol(25) | ◎ |
| Example 10-31 | 244cb(75)/acetone(25) | ◎ |
| Example 10-32 | 244cb(75)/trichloroethylene(25) | ◎ |
| Example 10-33 | 244cb(75)/ethyl acetate(25) | ○ |

The value in the bracket ( ) represents a proportion (% by weight)
Evaluation Standards
◎ Excellent
○ Good
△ Slight non-uniformity observed
X Substantial non-uniformity observed

TABLE 10-3

| | Diluents | Film forming properties |
|---|---|---|
| Example 10-34 | R226ca (100) | ◎ |
| Example 10-35 | R226cb (100) | ◎ |
| Example 10-36 | R222c (100) | ◎ |
| Example 10-37 | R223ca (100) | ◎ |
| Example 10-38 | R223cb (100) | ◎ |
| Example 10-39 | R224cc (100) | ◎ |
| Example 10-40 | R232ca (100) | ◎ |
| Example 10-41 | R232cb (100) | ◎ |
| Example 10-42 | R233cb (100) | ◎ |
| Example 10-43 | R233ca (100) | ◎ |
| Example 10-44 | R233cc (100) | ◎ |
| Example 10-45 | R242cb (100) | ◎ |
| Example 10-46 | R242ca (100) | ◎ |
| Example 10-47 | R226ca(75)/n-heptane(25) | ◎ |
| Example 10-48 | R226ca(75)/ethanol(25) | ◎ |
| Example 10-49 | 226ca(75)/acetone(25) | ◎ |
| Example 10-50 | 226ca(75)/trichloroethylene(25) | ◎ |

TABLE 10-3-continued

| | Diluents | Film forming properties |
|---|---|---|
| Example 10-51 | 226ca(75)/ethyl acetate(25) | ◎ |

The value in the bracket ( ) represents a proportion (% by weight)
Evaluation Standards
◎ Excellent
○ Good
△ Slight non-uniformity observed
X Substantial non-uniformity observed

EXAMPLES 11-1 to 11-51

A composition prepared by mixing 3 parts of the solvent composition as identified in Tables 11-1 to 11-3, 9.4 parts of pure water, 0.4 part of a surfactant, 1.6 parts of isopropyl myristate, 0.4 part of talc powder, 0.2 part of a perfume and 85 parts of a propellant (1,1-dichloro-2,2,2-trifluoroethane), was filled in an aerosol container and shaked a few times, whereupon the dispersibility of the aerosol composition was visually inspected. The results are shown in Tables 11-1 to 11-3.

TABLE 11-1

| | Solvent compositions | Dispersing effects |
|---|---|---|
| Example 11-1 | R224ca (100) | ◎ |
| Example 11-2 | R224cb (100) | ◎ |
| Example 11-3 | R225ca (100) | ◎ |
| Example 11-4 | R225cb (100) | ◎ |
| Example 11-5 | R234cc (100) | ◎ |
| Example 11-6 | R235cc (100) | ◎ |
| Example 11-7 | R243cc (100) | ◎ |
| Example 11-8 | R244ca (100) | ◎ |
| Example 11-9 | R252ca (100) | ◎ |
| Example 11-10 | R252cb (100) | ◎ |
| Example 11-11 | R262ca (100) | ◎ |
| Example 11-12 | R225ca(75)/n-heptane(25) | ◎ |
| Example 11-13 | R225ca(75)/ethanol(25) | ◎ |
| Example 11-14 | 225ca(75)/acetone(25) | ◎ |
| Example 11-15 | 225ca(75)/trichloroethylene(25) | ◎ |
| Example 11-16 | 225ca(75)/ethyl acetate(25) | ◎ |

The value in the bracket ( ) represents a proportion (% by weight)
Evaluation Standards
◎ Uniformly dispersed
○ Substantially uniformly dispersed
△ Slight non-uniformity observed
X Substantial non-uniformity observed

TABLE 11-2

| | Solvent compositions | Dispersing effects |
|---|---|---|
| Example 11-17 | R225cc (100) | ◎ |
| Example 11-18 | R234ca (100) | ◎ |
| Example 11-19 | R234cb (100) | ◎ |
| Example 11-20 | R234cd (100) | ◎ |
| Example 11-21 | R235cb (100) | ◎ |
| Example 11-22 | R235cc (100) | ◎ |
| Example 11-23 | R243ca (100) | ◎ |
| Example 11-24 | R243cb (100) | ◎ |
| Example 11-25 | R244cb (100) | ◎ |
| Example 11-26 | R244cc (100) | ◎ |
| Example 11-27 | R253ca (100) | ◎ |
| Example 11-28 | R253cb (100) | ◎ |
| Example 11-29 | R244cb(75)/n-heptane(25) | ◎ |
| Example 11-30 | R244ca(75)/ethanol(25) | ◎ |
| Example 11-31 | 244cb(75)/acetone(25) | ◎ |
| Example 11-32 | 244cb(75)/trichloroethylene(25) | ◎ |
| Example 11-33 | 244cb(75)/ethyl acetate(25) | ◎ |

The value in the bracket ( ) represents a proportion (% by weight)
Evaluation Standards
◎ Uniformly dispersed
○ Substantially uniformly dispersed
△ Slight non-uniformity observed
X Substantial non-uniformity observed

TABLE 11-2

| | Solvent compositions | Dispersing effects |
|---|---|---|
| Example 11-34 | R226ca (100) | ◎ |
| Example 11-35 | R226cb (100) | ◎ |
| Example 11-36 | R222c (100) | ◎ |
| Example 11-37 | R223ca (100) | ◎ |
| Example 11-38 | R223cb (100) | ◎ |
| Example 11-39 | R224cc (100) | ◎ |
| Example 11-40 | R232ca (100) | ◎ |
| Example 11-41 | R232cb (100) | ◎ |
| Example 11-42 | R233cb (100) | ◎ |
| Example 11-43 | R233ca (100) | ◎ |
| Example 11-44 | R223cc (100) | ◎ |
| Example 11-45 | R242cb (100) | ◎ |
| Example 11-46 | R242ca (100) | ◎ |
| Example 11-47 | R226ca(75)/n-heptane(25) | ◎ |
| Example 11-48 | R226ca(75)/ethanol(25) | ◎ |
| Example 11-49 | 226ca(75)/acetone(25) | ◎ |
| Example 11-50 | 226ca(75)/trichloroethylene(25) | ◎ |
| Example 11-51 | 226cb(75)/ethyl acetate(25) | ◎ |

The value in the bracket ( ) represents a proportion (% by weight)
Evaluation Standards
◎ Uniformly dispersed
○ Substantially uniformly dispersed
△ Slight non-uniformity observed
X Substantial non-uniformity observed

EXAMPLES 12-1 to 12-11

The most important insulating property among the properties of an insulating medium is a volume resistivity. It is generally accepted that a medium is useful as an insulating medium if it has a volume resistivity of at least $10^{13}$ Ωcm.

The volume resistivity values of insulating medium compositions of the present invention are shown in Table 12, wherein in each case, the volume resistivity meets the above standard.

TABLE 12

| | Insulating media | Volume resistivity |
|---|---|---|
| Example 12-1 | R224ca | ◎ |
| Example 12-2 | R224cb | ◎ |
| Example 12-3 | R225ca | ◎ |
| Example 12-4 | R225cb | ◎ |
| Example 12-5 | R234cc | ◎ |
| Example 12-6 | R235ca | ◎ |
| Example 12-7 | R243cc | ◎ |
| Example 12-8 | R244ca | ◎ |
| Example 12-9 | R252ca | ◎ |
| Example 12-10 | R252cb | ◎ |
| Example 12-11 | R262ca | ◎ |

◎ Volume resistivity of at least $1 \times 10^{13}$ Ωcm.

The novel halogenated hydrocarbon solvents of the present invention are excellent in that the power for destroying ozone is extremely small as compared with R113 which has been commonly used as a solvent, and the toxicity is lower than the conventional chlorinated hydrocarbon solvent such as trichloroethylene or perchloroethylene, whereby there will be no substantial problem of pollution of underground water.

Further, when employed for various purposes, they are capable of providing substantially equal or even higher performance as compared with conventional R113 or chlorinated hydrocarbon solvents.

What is claimed is:

1. A method of cleaning a surface of a substrate which comprises treating said surface with a solvent comprising a compound of the formula 1,1-dichloro-2,2,3,3-pentafluoropropane.

2. A method of cleaning a surface of a substrate which comprises treating said surface with a solvent comprising a compound of the formula 1,3-dichloro-1,1,2,2,3-pentafluoropropane.

* * * * *

UNITED STATES PATENT AND TRADEMARK OFFICE
CERTIFICATE OF CORRECTION

PATENT NO. : 5,116,426
DATED : May 26, 1992
INVENTOR(S) : Teruo Asano et al.

It is certified that error appears in the above-identified patent and that said Letters Patent is hereby corrected as shown below:

On title page,

Item[73], should be, --Asahi Glass Company Ltd., Tokyo, Japan--.

Signed and Sealed this

Thirteenth Day of July, 1993

Attest:

MICHAEL K. KIRK

Attesting Officer

Acting Commissioner of Patents and Trademarks